(12) United States Patent
Minagawa (10) Patent No.: US 10,189,944 B2
(45) Date of Patent: Jan. 29, 2019

(54) SURFACE MODIFICATION METHOD AND SURFACE-MODIFIED ELASTIC BODY

(71) Applicant: SUMITOMO RUBBER INDUSTRIES, LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 967 days.

(21) Appl. No.: 14/260,358

(22) Filed: Apr. 24, 2014

(65) Prior Publication Data

US 2014/0322468 A1 Oct. 30, 2014

(30) Foreign Application Priority Data

Apr. 25, 2013 (JP) .................................. 2013-092843

(51) Int. Cl.
*C08G 69/48* (2006.01)
*C08J 3/28* (2006.01)
(Continued)

(52) U.S. Cl.
CPC ............ *C08G 69/48* (2013.01); *A61L 29/085* (2013.01); *A61L 29/14* (2013.01); *C08F 2/48* (2013.01);
(Continued)

(58) Field of Classification Search
CPC ...... C08J 7/18; C08J 2300/26; C08J 2300/22; C08F 2/48; C08L 33/08; A61L 29/14; A61L 29/085
(Continued)

(56) References Cited

U.S. PATENT DOCUMENTS 3,418,066 A 12/1968 Caldwell et al.
5,100,689 A 3/1992 Goldberg et al.
(Continued)

FOREIGN PATENT DOCUMENTS

CN 101372538 A 2/2009
CN 101565489 A 10/2009
(Continued)

OTHER PUBLICATIONS

Allmér et al., "Surface Modification of Polymers. I. Vapour Phase Photografting with Acrylic Acid," Journal of Polymer Science: Part A: Polymer Chemistry, vol. 26, 1988, pp. 2099-2111.
(Continued)

*Primary Examiner* — Sanza L. McClendon
(74) *Attorney, Agent, or Firm* — Birch, Stewart, Kolasch & Birch, LLP (57) ABSTRACT

Provided are methods for surface-modifying a rubber vulcanizate or a thermoplastic elastomer, the methods forming a surface with a chemically fixed lubricant instead of resin coating which has drawbacks, such as that the coating is, for example, removed or peeled during the movement within a vessel, whereby the lubricity is reduced. The present invention relates to a method for surface-modifying an object of a rubber vulcanizate or a thermoplastic elastomer, the method including step 1 of forming polymerization initiation points on a surface of the object, and step 2 of radically polymerizing a deliquescent monomer starting from the polymerization initiation points by irradiation with ultraviolet light having a wavelength within the range of 300 to 400 nm, to grow polymer chains on the surface of the object.

16 Claims, 1 Drawing Sheet

(51) Int. Cl.
  *C08F 2/52*     (2006.01)
  *A61L 29/08*    (2006.01)
  *A61L 29/14*    (2006.01)
  *C08F 2/48*     (2006.01)
  *C08J 7/18*     (2006.01)

(52) U.S. Cl.
  CPC .............. *C08J 7/18* (2013.01); *A61L 2400/10* (2013.01); *C08J 2300/22* (2013.01); *C08J 2300/26* (2013.01); *Y10T 428/1386* (2015.01); *Y10T 428/24479* (2015.01)

(58) Field of Classification Search
  USPC ..................................... 522/96, 90, 135, 182
  See application file for complete search history.

(56) References Cited

U.S. PATENT DOCUMENTS

| | | |
|---|---|---|
| 5,154,727 A | 10/1992 | Dyer |
| 5,340,879 A | 8/1994 | Audenaert et al. |
| 5,453,467 A | 9/1995 | Bamford et al. |
| 5,637,460 A | 6/1997 | Swan et al. |
| 5,688,252 A | 11/1997 | Matsuda et al. |
| 5,855,623 A | 1/1999 | English et al. |
| 5,885,566 A | 3/1999 | Goldberg |
| 5,889,073 A | 3/1999 | Zhang et al. |
| 5,967,714 A | 10/1999 | Ottersbach et al. |
| 6,001,894 A | 12/1999 | Ottersbach et al. |
| 6,188,075 B1 | 2/2001 | Takayama et al. |
| 6,203,856 B1 | 3/2001 | Ottersbach et al. |
| 6,228,172 B1 | 5/2001 | Taylor et al. |
| 6,358,557 B1 | 3/2002 | Wang et al. |
| 6,808,738 B2 | 10/2004 | Ditizio et al. |
| 7,348,055 B2 | 3/2008 | Chappa et al. |
| 8,299,139 B1 | 10/2012 | Taranekar et al. |
| 8,323,750 B2 | 12/2012 | Yang et al. |
| 8,840,927 B2 | 9/2014 | Ditizio et al. |
| 9,339,845 B2 | 5/2016 | Minagawa |
| 9,469,736 B2 * | 10/2016 | Minagawa .............. A63C 5/056 |
| 9,758,605 B2 | 9/2017 | Minagawa |
| 2002/0161065 A1 | 10/2002 | Ditizio et al. |
| 2004/0086568 A1 | 5/2004 | Ditizio et al. |
| 2004/0106732 A1 | 6/2004 | Tsuji et al. |
| 2005/0137355 A1 | 6/2005 | Buckanin et al. |
| 2006/0155057 A1 | 7/2006 | Hermeling et al. |
| 2007/0003592 A1 | 1/2007 | Hissink |
| 2007/0116971 A1 | 5/2007 | Yoshikawa et al. |
| 2008/0016644 A1 | 1/2008 | Mizote et al. |
| 2008/0103287 A1 | 5/2008 | Chino et al. |
| 2008/0312377 A1 | 12/2008 | Schmidt et al. |
| 2009/0169715 A1 | 7/2009 | Dias et al. |
| 2009/0239089 A1 | 9/2009 | Agata et al. |
| 2010/0255336 A1 | 10/2010 | Zabinski |
| 2011/0124766 A1 | 5/2011 | Yang et al. |
| 2011/0160357 A1 | 6/2011 | Gerster et al. |
| 2011/0274940 A1 | 11/2011 | Kyomoto et al. |
| 2012/0021151 A1 | 1/2012 | Tatarka et al. |
| 2012/0100369 A1 | 4/2012 | Hanazawa et al. |
| 2013/0203883 A1 | 8/2013 | Minagawa |
| 2013/0274367 A1 | 10/2013 | Minagawa et al. |
| 2013/0310772 A1 | 11/2013 | Minagawa |
| 2014/0039084 A1 | 2/2014 | Minagawa |
| 2014/0128493 A1 | 5/2014 | Minagawa |
| 2014/0322468 A1 | 10/2014 | Minagawa |
| 2015/0203612 A1 | 7/2015 | Minagawa |

FOREIGN PATENT DOCUMENTS

| | | |
|---|---|---|
| CN | 102382291 A | 3/2012 |
| CN | 202427397 U | 9/2012 |
| CN | 103242553 A | 8/2013 |
| CN | 104119552 A | 10/2014 |
| EP | 0 872 512 A2 | 10/1998 |
| EP | 2 623 335 A2 | 8/2013 |
| EP | 2 664 627 A1 | 11/2013 |
| EP | 2 796 155 A1 | 10/2014 |
| EP | 2 894 191 A | 7/2015 |
| GB | 1120803 A | 7/1968 |
| GB | 1120804 A | 7/1968 |
| JP | 60-221410 A | 11/1985 |
| JP | 61-209667 A | 9/1986 |
| JP | 62-87163 A | 4/1987 |
| JP | 63-92658 A | 4/1988 |
| JP | 5-43634 A | 2/1993 |
| JP | 5-76590 A | 3/1993 |
| JP | 5-179055 A | 7/1993 |
| JP | 6-25450 A | 2/1994 |
| JP | 6-510322 A | 11/1994 |
| JP | 7-100744 B2 | 11/1995 |
| JP | 8-1793 A | 1/1996 |
| JP | 9-31361 A | 2/1997 |
| JP | 9-67457 A | 3/1997 |
| JP | 9-108359 A | 4/1997 |
| JP | 9-313594 A | 12/1997 |
| JP | 10-90500 A | 4/1998 |
| JP | 10-251350 A | 9/1998 |
| JP | 10-298320 A | 11/1998 |
| JP | 11-192305 A | 7/1999 |
| JP | 2000-273229 A | 10/2000 |
| JP | 2001-31871 A | 2/2001 |
| JP | 2001-46956 A | 2/2001 |
| JP | 2001-95621 A | 4/2001 |
| JP | 2002-145971 A | 5/2002 |
| JP | 2002-544346 A | 12/2002 |
| JP | 2003-2903 A | 1/2003 |
| JP | 2003-510378 A | 3/2003 |
| JP | 2004-528418 A | 9/2004 |
| JP | 2004-298220 A | 10/2004 |
| JP | 2005-516736 A | 6/2005 |
| JP | 2005-213516 A | 8/2005 |
| JP | 2005-523981 A | 8/2005 |
| JP | 2005-253538 A | 9/2005 |
| JP | 2007-77286 A | 3/2007 |
| JP | 2007-119563 A | 5/2007 |
| JP | 2007-145884 A | 6/2007 |
| JP | 2007-514861 A | 6/2007 |
| JP | 2007-202965 A | 8/2007 |
| JP | 2009-30074 A | 2/2009 |
| JP | 2009-518479 A | 5/2009 |
| JP | 2009-138169 A | 6/2009 |
| JP | 2009-226718 A | 10/2009 |
| JP | 2009-227842 A | 10/2009 |
| JP | 2010-23710 A | 2/2010 |
| JP | 2010-142537 A | 7/2010 |
| JP | 2010-142573 A | 7/2010 |
| JP | 2010-150349 A | 7/2010 |
| JP | 4523532 B2 | 8/2010 |
| JP | 2010-216964 A | 9/2010 |
| JP | 2011-42755 A | 3/2011 |
| JP | 2011-67362 A | 4/2011 |
| JP | 2011-188908 A | 9/2011 |
| JP | 2011-189562 A | 9/2011 |
| JP | 2011-208133 A | 10/2011 |
| JP | 2011-219520 A | 11/2011 |
| JP | 2011-241190 A | 12/2011 |
| JP | 2012-105579 A | 6/2012 |
| JP | 2012-162646 A | 8/2012 |
| JP | 2013-159629 A | 8/2013 |
| JP | 2013-159667 A | 8/2013 |
| JP | 2013-208777 A | 10/2013 |
| JP | 2013-237801 A | 11/2013 |
| JP | 2013-237802 A | 11/2013 |
| JP | 2014-31429 A | 2/2014 |
| JP | 2014-31430 A | 2/2014 |
| JP | 2014-108153 A | 6/2014 |
| WO | WO 93/05081 A1 | 3/1993 |
| WO | WO 03/068289 A1 | 8/2003 |
| WO | WO 03/093357 A1 | 11/2003 |
| WO | WO 2007/065721 A2 | 6/2007 |
| WO | WO 2007/072613 A1 | 6/2007 |
| WO | WO 2010/058848 A1 | 5/2010 |
| WO | WO 2010/131652 A1 | 11/2010 |

(56) References Cited

FOREIGN PATENT DOCUMENTS

| WO | WO 2011/038483 A1 | 4/2011 |
|---|---|---|
| WO | WO 2012/091169 A1 | 7/2012 |
| WO | WO 2012/165525 A1 | 12/2012 |

OTHER PUBLICATIONS

International Search Report issued in PCT/JP2013/074219 dated Dec. 3, 2013.

International Search Report, dated Jul. 24, 2012, for International Application No. PCT/JP2012/064030.

U.S. Non-Final Office Action, dated May 8, 2015, for U.S. Appl. No. 13/756,837.

U.S. Non-Final Office Action, dated Oct. 20, 2014, for U.S. Appl. No. 13/756,837.

U.S. Notice of Allowance, dated Dec. 26, 2014, for U.S. Appl. No. 13/956,974.

U.S. Office Action (Requirement for Restriction/Election), dated May 9, 2014, for U.S. Appl. No. 13/956,974.

U.S. Office Action dated Jun. 24, 2015, for U.S. Appl. No. 14/118,136.

U.S. Office Action dated Sep. 21, 2015, for U.S. Appl. No. 14/107,746.

U.S. Office Action, dated Apr. 17, 2015, for U.S. Appl. No. 13/775,451.

U.S. Office Action, dated Aug. 25, 2014, for U.S. Appl. No. 13/956,974.

International Search Report and Written Opinion of the International Searching Authority, issued in PCT/JP2014/079947, dated Jan. 20, 2015.

International Search Report, dated Feb. 25, 2014, for International Application No. PCT/JP2013/082409.

International Search Report, issued in PCT/JP2014/063268, dated Aug. 19, 2014.

U.S. Office Action, dated Nov. 3, 2016, for U.S. Appl. No. 14/896,096.

"Fundamental of Polymer Chemistry and Physics," edited by Wuji Wei and etc., Chemical Industry Press, Oct. 2011, pp. 59-60 (4 pages total).

English translation of the Chinese Office Action, dated Sep. 22, 2017, for Chinese Application No. 201380044153.X.

International Search Report and English translation thereof, dated Jan. 21, 2014, for International Application No. PCT/JP2013/081090.

Jinan Haohua Industry Co., Ltd., "Ethanaminum, N,N,N-trimethyl-2-[(2-methyl-1-oxo-2-propen-1-yl)oxy]-, chloride (1:1)," CAS: 5039-78-1, Product Information Inquiry Description, found online on Dec. 27, 2016, pp. 1-2 (3 pages), http://guide7932.guidechem.com/pro-show2436647.html.

English translation of Chinese Office Action for Appl. No. 201480032195.6 dated Jan. 24, 2018.

Zhang, J., et al, "Corona Radiation Technology" China Textile Press, May 2003, p. 14.

International Search Report (Form PCT/ISA/210) for International Application No. PCT/JP2014/082367, dated Mar. 3, 2015, with an English translation.

Written Opinion of the International Searching Authority (Form PCT/ISA/237) for International Application No. PCT/JP2014/082367, dated Mar. 3, 2015, with an English translation.

* cited by examiner

SURFACE MODIFICATION METHOD AND SURFACE-MODIFIED ELASTIC BODY

TECHNICAL FIELD

The present invention relates to methods for surface modification providing a surface having lubricity when wetted; and surface-modified elastic bodies at least partially having a surface modified by the surface modification method, such as medical devices and catheters.

BACKGROUND ART

Catheters used in the medical field and the like, such as vascular catheters, and urethral catheters for urethral catheterization, are inserted into blood vessels, digestive tracts, tracheae, bile ducts, or ureters and used in aqueous solutions such as blood and body fluids. Catheters are thus required to be able to be smoothly inserted without damaging tissues.

In this context, a low friction lubricant is applied to the surface of a catheter, or the surface is coated with a lubricant layer, before use (see Patent Literatures 1 to 3).

However, these methods have drawbacks in that the surfaces formed by these methods have insufficient lubricity, and that since the lubricants are not chemically fixed on the surfaces of catheters, they are, for example, removed or peeled during the movement within a vessel, whereby the lubricity is reduced.

CITATION LIST

Patent Literature

Patent Literature 1: JP 2011-188908 A
Patent Literature 2: JP 2009-518479 T
Patent Literature 3: JP H07-100744 B

SUMMARY OF INVENTION

Technical Problem

The present invention aims to solve the aforementioned problems to provide methods for surface-modifying a rubber vulcanizate or a thermoplastic elastomer, the methods forming a surface with a chemically fixed lubricant instead of resin coating which has drawbacks, such as that the coating is, for example, removed or peeled during the movement within a vessel, whereby the lubricity is reduced. The present invention also aims to provide surface-modified elastic bodies, such as fenders and medical devices (e.g. catheters), each at least partially having a surface modified by the surface modification method.

Solution to Problem

The present invention relates to a method for surface-modifying an object of a rubber vulcanizate or a thermoplastic elastomer, the method including: step 1 of forming polymerization initiation points on a surface of the object; and step 2 of radically polymerizing a deliquescent monomer starting from the polymerization initiation points by irradiation with ultraviolet light having a wavelength within the range of 300 to 400 nm, to grow polymer chains on the surface of the object.

The present invention relates to a method for surface-modifying an object of a rubber vulcanizate or a thermoplastic elastomer, the method including step I of radically polymerizing a deliquescent monomer in the presence of a photopolymerization initiator by irradiation with ultraviolet light having a wavelength within the range of 300 to 400 nm, to grow polymer chains on a surface of the object.

The step 1 preferably includes adsorbing a photopolymerization initiator on the surface of the object, and optionally then irradiating the surface with ultraviolet light having a wavelength within the range of 300 to 400 nm, to form the polymerization initiation points from the photopolymerization initiator on the surface.

The photopolymerization initiator is preferably at least one of a benzophenone compound and a thioxanthone compound.

The method preferably includes inserting an inert gas into a reaction container, a reaction tube, and a reaction solution during or before the light irradiation, and polymerizing the monomer in an atmosphere replaced with the inert gas.

The deliquescent monomer is preferably an alkali metal-containing monomer.

The alkali metal-containing monomer is preferably at least one selected from the group consisting of alkali metal salts of acrylic acid, methacrylic acid, itaconic acid, 3-vinylpropionic acid, vinylsulfonic acid, 2-sulfoethyl (meth)acrylate, 3-sulfopropyl(meth)acrylate, 2-acrylamide-2-methylpropanesulfonic acid, or styrenesulfonic acid.

The deliquescent monomer is preferably at least one selected from the group consisting of zwitterionic monomers and alkali metal-containing monomers.

Preferably, the (liquid) deliquescent monomer or a solution thereof contains a polymerization inhibitor, and is polymerized in the presence of the polymerization inhibitor. The polymerization inhibitor is preferably 4-methylphenol.

The polymer chains preferably each have a length within the range of 10 to 50000 nm.

The present invention relates to a surface-modified elastic body, formed by the surface modification method.

The present invention relates to a surface-modified elastic body, which is formed by the surface modification method and is required to have lubricity in the presence of water.

The present invention relates to a surface-modified elastic body, including a three-dimensional solid at least partially having a surface modified by the surface modification method.

The surface-modified elastic body is preferably a polymer brush.

The present invention relates to a catheter, at least partially having a surface modified by the surface modification method.

The present invention also relates to a fender, at least partially having a groove surface modified by the surface modification method.

Advantageous Effects of Invention

The present invention provides a method for surface-modifying an object of a rubber vulcanizate or a thermoplastic elastomer, including step 1 of forming polymerization initiation points on a surface of the object, and step 2 of radically polymerizing a deliquescent monomer starting from the polymerization initiation points by irradiation with ultraviolet light having a wavelength within the range of 300 to 400 nm, to grow polymer chains on the surface of the object; and also provides a method for surface-modifying an object of a rubber vulcanizate or a thermoplastic elastomer, including step I of radically polymerizing a deliquescent monomer in the presence of a photopolymerization initiator by irradiation with ultraviolet light having a wavelength within the range of 300 to 400 nm, to grow polymer chains on a surface of the object. Thus, a polymer with lubricity is fixed on the surface of the object, which makes it possible to provide excellent lubricity and also to provide lubricant durability after repeated movements, or in other words, durability that is so high that there will be little reduction in lubricity. Thus, forming polymer chains on the surface of the object to be modified by the method enables to provide a surface-modified elastic body such as a catheter or a fender, which is excellent in those properties.

DESCRIPTION OF EMBODIMENTS

Figure 1:
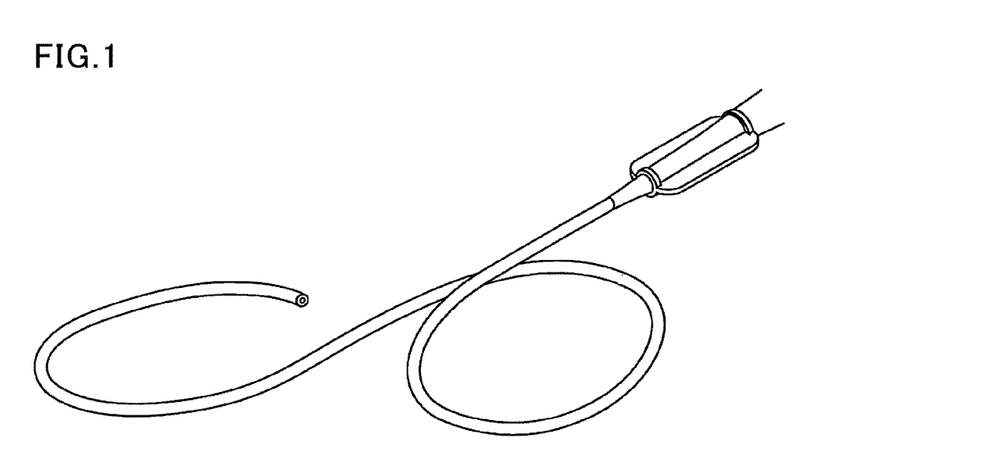
FIG. 1 is a schematic view of an example of a vascular catheter.
Figure 2:
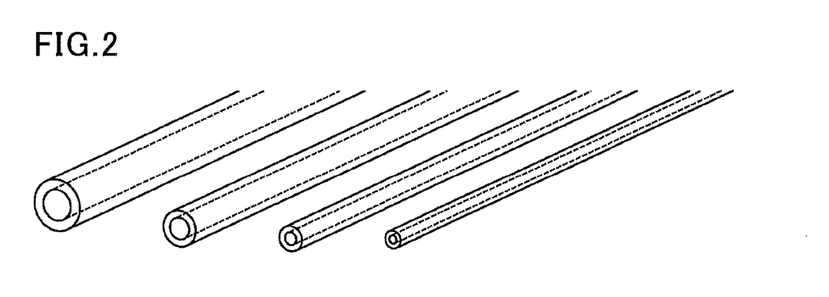
FIG. 2 is a schematic view showing examples of catheters with different diameters.

The present invention includes a method for surface-modifying an object of a rubber vulcanizate or a thermoplastic elastomer, including step 1 of forming polymerization initiation points on a surface of the object, and step 2 of radically polymerizing a deliquescent monomer starting from the polymerization initiation points by irradiation with ultraviolet light having a wavelength within the range of 300 to 400 nm, to grow polymer chains on the surface of the object.

In step 1, polymerization initiation points are formed on a surface of a molded rubber vulcanizate or a molded thermoplastic elastomer (the object to be modified). For example, the step 1 may be performed by adsorbing a photopolymerization initiator on the surface of the object to form the polymerization initiation points, or by adsorbing a photopolymerization initiator on the surface of the object and then irradiating the surface with ultraviolet light having a wavelength within the range of 300 to 400 nm to form the polymerization initiation points from the photopolymerization initiator on the surface.

Examples of thermoplastic elastomers that can be used as the object to be modified include nylon, polyester, polyurethane, polypropylene, ABS (acrylonitrile-butadiene-styrene copolymer resin), fluororesins such as polytetrafluoroethylene, and dynamically crosslinked thermoplastic elastomers of these. Specific examples of nylon include nylon 6, nylon 66, nylon 11, and nylon 12. The dynamically crosslinked thermoplastic elastomer is preferably one obtained by dynamically crosslinking a halogenated butyl rubber in a thermoplastic elastomer. This thermoplastic elastomer is preferably nylon, polyurethane, polypropylene, SIBS (styrene-isobutylene-styrene block copolymer), or the like.

Examples of rubbers that can be used as the object to be modified include natural rubber, deproteinized natural rubber, styrene butadiene rubber, butadiene rubber, isoprene rubber, silicone rubber, and butyl rubber and halogenated butyl rubber which contain a few percent of isoprene units, calculated as the degree of unsaturation.

The vulcanization conditions of the rubber may be appropriately set, and the vulcanization temperature of the rubber is preferably 140° C. or higher, more preferably 170° C. or higher, and still more preferably 175° C. or higher.

Examples of the photopolymerization initiators include carbonyl compounds, organic sulfur compounds such as tetraethylthiuram disulfide, persulfides, redox compounds, azo compounds, diazo compounds, halogen compounds, and photoreducing dyes. Preferred among these are carbonyl compounds.

The carbonyl compound as a photopolymerization initiator is preferably benzophenone or a derivative thereof (a benzophenone compound). For example, it may suitably be a benzophenone compound represented by the following formula.

In the formula, $R^1$ to $R^5$ and $R^{1'}$ to $R^{5'}$ are the same as or different from one another and each represent a hydrogen atom, an alkyl group, a halogen (fluorine, chlorine, bromine or iodine), a hydroxyl group, a primary to tertiary amino group, a mercapto group, or a hydrocarbon group that may contain an oxygen, nitrogen, or sulfur atom, provided that any two adjacent groups thereof may be joined to each other to form a ring together with the carbon atoms to which they are bonded.

Specific examples of the benzophenone compound include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Particularly preferred among these are benzophenone, xanthone, and 9-fluorenone, in terms of providing a good polymer brush.

The photopolymerization initiator may also suitably be a thioxanthone compound because it provides a high polymerization rate and can easily be adsorbed on and/or reacted with rubber or the like. For example, it may suitably be a compound represented by the following formula.

In the formula, $R^6$ to $R^9$ and $R^{6'}$ to $R^{9'}$ are the same as or different from one another and each represent a hydrogen atom, a halogen atom, or an alkyl, cyclic alkyl, aryl, alkenyl, alkoxy, or aryloxy group.

Examples of the thioxanthone compounds represented by the above formula include thioxanthone, 2-isopropylthioxanthone, 4-isopropylthioxanthone, 2,3-diethylthioxanthone, 2,4-diethylthioxanthone, 2,4-dichlorothioxanthone, 2-methoxythioxanthone, 1-chloro-4-propoxythioxanthone, 2-cyclohexylthioxanthone, 4-cyclohexylthioxanthone, 2-vinylthioxanthone, 2,4-divinylthioxanthone, 2,4-diphenylthioxanthone, 2-butenyl-4-phenylthioxanthone, 2-methoxythioxanthone, and 2-p-octyloxyphenyl-4-ethylthioxanthone. Preferred among these are those in which one or two of the groups $R^6$ to $R^9$ and $R^{6'}$ to $R^{9'}$, especially two of them, are each substituted with an alkyl group. More preferred is 2,4-diethylthioxanthone.

The adsorption of a photopolymerization initiator (e.g. a benzophenone or thioxanthone compound) onto the surface of the object to be modified may be performed as follows. In the case of using a benzophenone or thioxanthone compound, for example, the benzophenone or thioxanthone compound is dissolved in an organic solvent to prepare a solution; a surface portion of the object to be modified is treated with this solution so that the compound is adsorbed on the surface portion; and, if necessary, the organic solvent is dried and evaporated off, whereby polymerization initiation points are formed. The surface-treating method may be any method that allows the solution of the benzophenone or thioxanthone compound to be brought into contact with the surface of the object to be modified. Suitable methods include applying or spraying the benzophenone or thioxanthone compound solution onto the surface; or, alternatively, immersing the surface into the solution. If only a part of the surface needs to be modified, it is sufficient to adsorb the photopolymerization initiator only onto the necessary part of the surface. In this case, for example, application or spraying of the solution is suitable. Examples of the solvents include methanol, ethanol, acetone, benzene, toluene, methyl ethyl ketone, ethyl acetate, and THF. Acetone is preferred because it does not swell the object and it can be rapidly dried and evaporated off.

As described, after the photopolymerization initiator is adsorbed on the surface of the object, the surface may be then irradiated with ultraviolet light having a wavelength within the range of 300 to 400 nm to form the polymerization initiation points from the photopolymerization initiator on the surface. This irradiation with ultraviolet light may be performed by a known method, for example, by the same method as in step 2 described later.

In step 2, a deliquescent monomer is radically polymerized starting from the polymerization initiation points formed in step 1, by irradiation with ultraviolet light having a wavelength within the range of 300 to 400 nm, to grow polymer chains on the surface of the object.

The deliquescent monomer refers to a monomer having deliquescent properties, that is, a monomer that automatically captures moisture (water vapor) in the air to form an aqueous solution. The deliquescent monomer may suitably be, for example, an alkali metal-containing monomer (a monomer containing an alkali metal within the molecule) or a zwitterionic monomer (a zwitterionic group-containing compound, i.e., a compound having both a center of permanent positive charge and a center of negative charge). These monomers may be used alone, or two or more thereof may be used in combination.

Examples of the alkali metal-containing monomers include alkali metal salts of acrylic acid (e.g. sodium acrylate, potassium acrylate); alkali metal salts of methacrylic acid (e.g. sodium methacrylate, potassium methacrylate); alkali metal salts of itaconic acid (e.g. sodium itaconate, potassium itaconate); alkali metal salts of 3-vinylpropionic acid (e.g. sodium 3-vinylpropionate, potassium 3-vinylpropionate); alkali metal salts of vinylsulfonic acid (e.g. sodium vinylsulfonate, potassium vinylsulfonate); alkali metal salts of 2-sulfoethyl(meth)acrylate (e.g. sodium 2-sulfoethyl(meth)acrylate, potassium 2-sulfoethyl(meth)acrylate); alkali metal salts of 3-sulfopropyl (meth)acrylate (e.g. sodium 3-sulfopropyl (meth)acrylate, potassium 3-sulfopropyl (meth)acrylate); alkali metal salts of 2-acrylamide-2-methylpropanesulfonic acid (e.g. sodium 2-acrylamide-2-methylpropanesulfonate, potassium 2-acrylamide-2-methylpropanesulfonate); and alkali metal salts of styrenesulfonic acid (e.g. sodium styrenesulfonate, potassium styrenesulfonate). Preferred among these is potassium 3-sulfopropyl methacrylate.

Examples of the zwitterionic monomers include carboxybetaines, sulfobetaines, and phosphobetaines. The zwitterionic monomer may also be a compound represented by the following formula (1), and particularly suitably a compound represented by formula (2) below.

(1)

In the formula, $R^{11}$ represents —H or —$CH_3$; X represents —O—, —NH—, or —$N^+$—; m denotes an integer of 1 or more; and Y represents a zwitterionic or halogen group (e.g., $Cl^-$, $Br^-$, or $F^-$).

In the formula (1), preferably, $R^{11}$ is —$CH_3$, X is —O—, and m is an integer of 1 to 10. In the zwitterionic group indicated by Y, the cation may be a quaternary ammonium such as a tetraalkylammonium; the anion may be a carboxylic acid, sulfonic acid, or phosphate.

(2)

In the formula, $R^{11}$ represents —H or —$CH_3$; p and q each denote an integer of 1 or more; and $Y^1$ and $Y^2$ represent ionic functional groups of opposite charge to each other.

In the formula (2), p is preferably an integer of 2 or more, and more preferably an integer of 2 to 10. The symbol q is preferably an integer of 1 to 10, and more preferably an integer of 2 to 4. $R^{11}$ is preferably as described hereinabove. The aforementioned cations and anions may be mentioned for $Y^1$ and $Y^2$.

Suitable typical examples of the zwitterionic monomer include compounds represented by the following formulae (2-1) to (2-4).

(2-1)

In the formula, $R^{11}$ represents a hydrogen atom or a methyl group; and p and q each denote an integer of 1 to 10.

(2-2)

In the formula, $R^{11}$ represents a hydrogen atom or a methyl group; and p and q each denote an integer of 1 to 10.

(2-3)

In the formula, $R^{11}$ represents a hydrogen atom or a methyl group; $R^{12}$ represents a C1 to C6 hydrocarbon group; and p and q each denote an integer of 1 to 10.

(2-4)

In the formula, $R^{11}$ represents a hydrogen atom or a methyl group; $R^{13}$, $R^{14}$, and $R^{15}$ are the same as or different from one another and each represent a C1 or C2 hydrocarbon group; and p and q each denote an integer of 1 to 10.

Examples of the compounds represented by the formula (2-1) include dimethyl(3-sulfopropyl)(2-(meth)acryloyloxyethyl)ammonium betaine. Examples of the compounds represented by the formula (2-2) include dimethyl(2-carboxyethyl)(2-(meth)acryloyloxyethyl)ammonium betaine. Examples of the compounds represented by the formula (2-3) include dimethyl(3-methoxy phosphopropyl)(2-(meth) acryloyloxyethyl)ammonium betaine. Examples of the compounds represented by the formula (2-4) include 2-(meth) acryloyloxyethyl phosphorylcholine. Other examples of the zwitterionic monomers include 2-(meth)acryloyloxyethyl carboxybetaine and 2-(meth)acryloyloxyethyl sulfobetaine. Particularly preferred among these is 2-(meth)acryloyloxyethyl phosphorylcholine because it has high biocompatibility, or in other words, low protein adsorbability.

The following describes an example of the method for radically polymerizing a deliquescent monomer in step 2. First, a (liquid) deliquescent monomer or a solution thereof is applied (sprayed) onto the surface of the object on which a benzophenone or thioxanthone compound or the like has been adsorbed. Or alternatively, the object is immersed in a (liquid) deliquescent monomer or a solution thereof. Then, the object is irradiated with ultraviolet light to allow radical polymerization (photo-radical polymerization) of the monomer to proceed to grow polymer chains on the surface of the object. Additionally, after the application, the surface of the object may be covered with a sheet of transparent glass, PET, polycarbonate or the like, followed by irradiation of the covered surface with light (e.g., ultraviolet light) to allow radical polymerization (photo-radical polymerization) of the monomer to proceed to grow polymer chains on the surface of the object.

The solvent for application (spraying), the method for application (spraying), the method for immersion, the conditions for irradiation, and the like may be conventionally known materials or methods. The solution of the radically polymerizable monomer may be an aqueous solution or a solution prepared by dissolving the monomer in an organic solvent that does not dissolve a photopolymerization initiator (e.g., a benzophenone or thioxanthone compound) to be used. Furthermore, the (liquid) radically polymerizable monomer or a solution thereof may contain a known polymerization inhibitor such as 4-methylphenol.

In the present invention, radical polymerization of the deliquescent monomer is allowed to proceed by light irradiation after the (liquid) deliquescent monomer or a solution thereof is applied to the surface, or after the surface is immersed in the (liquid) deliquescent monomer or a solution thereof. Here, ultraviolet light sources with an emission wavelength that is mainly in the ultraviolet region can be suitably used, such as high-pressure mercury lamps, metal halide lamps, and LED lamps. The light dose may be appropriately adjusted in consideration of the polymerization time and uniform progress of the reaction. In order to prevent the polymerization inhibition due to active gas like oxygen in a reaction container and a reaction tube, oxygen is preferably removed from the reaction container, the reaction tube, and the reaction solution during or before the light irradiation. Thus, some methods may appropriately be employed, for example, in which an inert gas like nitrogen gas or argon gas is inserted into the reaction container, the reaction tube, and the reaction solution to discharge active gas like oxygen from the reaction system, whereby the atmosphere in the reaction system is replaced with the inert gas. Moreover, in order to prevent the reaction inhibition due to oxygen or the like, some measures may appropriately be taken, for example, in which a ultraviolet light source is placed such that no air layer (oxygen content: 15% or higher) exists between the reaction container made of glass, plastics or the like, and the reaction solution or the object.

The ultraviolet light has a wavelength within the range of 300 to 400 nm. Such a wavelength enables the formation of good polymer chains on the surface of the object. Examples of light sources that can be used include high-pressure mercury lamps, LEDs with a center wavelength of 365 nm, and LEDs with a center wavelength of 375 nm. Irradiation with LED light having a wavelength within the range of 355 to 380 nm is more preferred. For example, LEDs with a center wavelength of 365 nm, which is close to the excitation wavelength (366 nm) of benzophenone, are particularly preferred in terms of efficiency. Light with a wavelength of shorter than 300 nm may damage the object by breaking the molecules thereof. Thus, light with a wavelength of 300 nm or longer is preferred, with light having a wavelength of 355 nm or longer being more preferred because it produces very little damage to the object. Light having a wavelength of longer than 400 nm, however, is less likely to activate the photopolymerization initiator, so that the polymerization reaction is not allowed to easily proceed. Thus, light having a wavelength of 400 nm or shorter is preferred. Although LED light is suitable in that it is in a narrow wavelength range and does not include light with other wavelengths than the center wavelength, a mercury lamp or the like can also achieve similar effects to LED light by using a filter to block light having a wavelength of shorter than 300 nm.

The present invention also relates to a method for surface-modifying an object of a rubber vulcanizate or a thermoplastic elastomer, including step I of radically polymerizing a deliquescent monomer in the presence of a photopolymerization initiator by irradiation with ultraviolet light having a wavelength within the range of 300 to 400 nm, to grow polymer chains on a surface of the object. More specifically, a deliquescent monomer is radically polymerized using a photopolymerization initiator as an initiator by irradiation with ultraviolet light, to form polymer chains, whereby a surface-modified elastic body can be prepared in which a polymer layer is formed on the surface of the object. In step I, the object to be modified, the photopolymerization initiator, and the deliquescent monomer used may be as described hereinabove.

For example, the step I may be performed by contacting a surface of the object with a photopolymerization initiator and a deliquescent monomer, and then irradiating the surface with LED light having a wavelength within the range of 300 to 400 nm, to form polymerization initiation points from the photopolymerization initiator while radically polymerizing the deliquescent monomer starting from the polymerization initiation points to grow polymer chains.

The following describes an example of the method for radically polymerizing a deliquescent monomer in step I. First, a (liquid) deliquescent monomer, or a solution thereof, containing a photopolymerization initiator (e.g., a benzophenone or thioxanthone compound) is applied (sprayed) onto a surface of the object. Or alternatively, the object is immersed in a (liquid) deliquescent monomer, or a solution thereof, containing a photopolymerization initiator. Then, the object is irradiated with light (e.g., ultraviolet light) to allow radical polymerization (photo-radical polymerization) of the monomer to proceed to grow polymer chains on the surface of the object. Additionally, the aforementioned method, in which the surface of the object is covered with a sheet of transparent glass, PET, polycarbonate or the like, followed by irradiation of the covered surface with light (e.g., ultraviolet light), may be employed. Here, the solvent for application (spraying), the method for application (spraying), the method for immersion, the conditions for irradiation, and the like may be as described hereinabove.

The polymer chains formed in step 2 or step I preferably each have a length within the range of 10 to 50000 nm, more preferably 100 to 50000 nm. Polymer chains shorter than 10 nm are unlikely to provide good lubricity. Polymer chains longer than 50000 nm are unlikely to further provide better lubricity, while they are likely to drive up the costs of raw materials because the monomer used is expensive. In addition, in such cases, surface patterns formed by the surface treatment are likely to be visible to the naked eye, which tends to spoil the appearance and to decrease the sealing properties.

In step 2 and step I, two or more kinds of monomers may be radically polymerized simultaneously. Moreover, multiple kinds of polymer chains may be grown on the surface of the object. The surface modification method of the present invention may include crosslinking between polymer chains. In this case, ionic crosslinking, or crosslinking by a hydrophilic group containing an oxygen atom, or crosslinking by a halogen group (e.g. iodine) may be performed between the polymer chains.

Treatment of a rubber vulcanizate or a thermoplastic elastomer by the surface modification method enables to provide a surface-modified elastic body. For example, a surface-modified elastic body that is excellent in lubricity in the presence of water can be obtained. Moreover, treatment of at least part of a three-dimensional solid (e.g. elastic body) by the above method enables to provide a surface-modified elastic body having better quality. Preferred examples of such a surface-modified elastic body include polymer brushes. The term "polymer brush" means an assembly of graft polymer chains obtained by the "grafting from" approach by surface-initiated living radical polymerization. The graft chains are preferably oriented in a direction substantially vertical to the surface of the object because, in such a case, the entropy is reduced and thus the molecular mobility of the graft chains is reduced, which ensures lubricity. Preferred are semidilute brushes and concentrated brushes, which have a brush density of 0.01 chains/nm$^2$ or higher.

Furthermore, treatment of a rubber vulcanizate or a thermoplastic elastomer by the surface modification method enables to prepare a medical device (e.g., a catheter) at least partially having a modified surface. The modification is preferably performed at least on a lubricity-requiring part of a surface of the medical device such as a catheter, or may be performed on the entire surface.

EXAMPLES

The present invention is more specifically described referring to examples in the following. The present invention is, however, not limited to these examples.

Example 1

A 3 wt % solution of benzophenone in acetone was applied to the surface of a thermoplastic elastomer tube made of nylon 12 to adsorb benzophenone, and then the surface was dried. Then, the tube was irradiated with LED light (5 mW/cm$^2$) with a wavelength of 365 nm for five minutes. During this period, the tube was rotated such that the entire surface was irradiated.

Subsequently, the tube was immersed in an aqueous solution of potassium 3-sulfopropyl methacrylate (1.25 M) in a glass reaction container. The container was sealed with a rubber stopper, and argon gas was inserted and allowed to bubble through the solution for 120 minutes to remove oxygen. The glass reaction container was irradiated with LED light with a wavelength of 365 nm for 60 minutes while being rotated. Thus, radical polymerization was carried out to grow polymer chains on the surface of the nylon tube, whereby a surface-modified elastic body (polymer brush) was prepared.

Example 2

A 3 wt % solution of benzophenone in acetone was applied to the surface of a thermoplastic elastomer tube made of nylon 12 to adsorb benzophenone, and then the surface was dried.

Then, the tube was immersed in an aqueous solution of potassium 3-sulfopropyl methacrylate (1.25 M) in a glass reaction container. The container was sealed with a rubber stopper, and argon gas was inserted and allowed to bubble through the solution for 120 minutes to remove oxygen. The glass reaction container was irradiated with LED light with a wavelength of 365 nm for 60 minutes while being rotated. Thus, radical polymerization was carried out to grow polymer chains on the surface of the nylon tube, whereby a surface-modified elastic body (polymer brush) was prepared.

Example 3

A 3 wt % solution of 2,4-diethylthioxanthone in acetone was applied to the surface of a thermoplastic elastomer tube made of nylon 12 to adsorb 2,4-diethylthioxanthone, and then the surface was dried.

Then, the tube was immersed in an aqueous solution of potassium 3-sulfopropyl methacrylate (1.25 M) in a glass reaction container. The container was sealed with a rubber stopper, and argon gas was inserted and allowed to bubble through the solution for 120 minutes to remove oxygen. The glass reaction container was irradiated with LED light with a wavelength of 365 nm for 40 minutes while being rotated. Thus, radical polymerization was carried out to grow polymer chains on the surface of the nylon tube, whereby a surface-modified elastic body (polymer brush) was prepared.

Example 4

A surface-modified elastic body (polymer brush) was prepared in the same manner as in Example 1, except that 2-methacryloyloxyethyl phosphorylcholine was used instead of potassium 3-sulfopropyl methacrylate.

Example 5

A surface-modified elastic body (a polymer brush in which polymer chains were grown on the surface of a polyurethane tube) was prepared in the same manner as in Example 1, except that a polyurethane tube was used instead of the nylon tube in Example 1.

Comparative Example 1

A tube made of nylon 12 was used as it was.

Comparative Example 2

Used was a tube made of nylon 12, the surface of which is coated with a 5% solution of methyl vinyl ether-maleic anhydride (GANTREZ-AN16, produced by ISP) in methanol. It should be noted that nylon 12 is a material often used for vascular catheters, and methyl vinyl ether-maleic anhydride is a typical lubricant for providing lubricity on the surfaces of vascular catheters.

The surface-modified elastic bodies prepared in the examples and the comparative examples were evaluated by the following methods.

(Length of Polymer Chain)

To determine the length of the polymer chain formed on the surface of the tube, a cross section of the tube with polymer chains was measured with a SEM at an accelerating voltage of 15 kV and a magnification of 1000 times. The thickness of the polymer layer in the photograph was measured and used as the length of the polymer chain.

(Lubricity)

Water was applied to the tube surface, and the sliding properties of the surface were then evaluated by a feeling test by human fingers. The feeling test was performed by ten evaluators according to the following rating scale of 1-5: a rating of 5 corresponds to a tube with good sliding properties and a rating of 1 corresponds to a tube with so poor sliding properties that fingers never slide on the surface. The average rating was calculated.

(Lubricant Durability)

After water was applied to the tube surface, the tube was held between fingers and moved by sliding on the fingers. This cycle was repeated 100 times. Then, a feeling test was again performed by ten evaluators according to the rating scale for lubricity, and the average rating and the rate of decrease from the initial lubricity were calculated.

Table 1 shows that the surfaces of the tubes in the examples each had high lubricity, good durability, and quite a low rate of decrease in lubricity. In contrast, Comparative Example 1, in which a tube was used as it was, had quite poor lubricity; Comparative Example 2, in which a commonly used product was used, had reasonably high initial lubricity, but had low durability and quite a high rate of decrease in lubricity.

These results demonstrated that forming polymer chains on the surface of a vascular catheter or the like using a deliquescent monomer such as potassium 3-sulfopropyl methacrylate or 2-methacryloyloxyethyl phosphorylcholine can simultaneously provide sufficient lubricity and lubricant durability.

The invention claimed is:

1. A method for producing a catheter of a rubber vulcanizate or a thermoplastic elastomer, the method comprising:
   step 1 of forming polymerization initiation points on a surface of the catheter; and
   step 2 of radically polymerizing a deliquescent monomer starting from the polymerization initiation points by irradiation with ultraviolet light having a wavelength within the range of 300 to 400 nm, to grow polymer chains on the surface of the catheter,
   wherein the deliquescent monomer is at least one selected from the group consisting of alkali metal salt of acrylic acid, alkali metal salt of methacrylic acid, alkali metal salt of itaconic acid, alkali metal salt of 3-vinylpropionic acid, alkali metal salt of 2-sulfoethyl (meth)acrylate, alkali metal salt of 3-sulfopropyl (meth)acrylate, alkali metal salt of 2-acrylamide-2-methylpropanesulfonic acid, and a compound represented by the following formula (1)

wherein $R^{11}$ represents —H or —$CH_3$; X represents —O—, —NH—, or —$N^+$—; m denotes an integer of one or more; and Y represents a zwitterionic or halogen group.

2. A method for producing a catheter of a rubber vulcanizate or a thermoplastic elastomer, the method comprising:
   step I of radically polymerizing a deliquescent monomer in the presence of a photopolymerization initiator by irradiation with ultraviolet light having a wavelength within the range of 300 to 400 nm, to grow polymer chains on a surface of the catheter,
   wherein the deliquescent monomer is at least one selected from the group consisting of alkali metal salt of acrylic acid, alkali metal salt of methacrylic acid, alkali metal salt of itaconic acid, alkali metal salt of 3-vinylpropionic acid, alkali metal salt of 2-sulfoethyl (meth)acrylate, alkali metal salt of 3-sulfopropyl (meth)acrylate,

TABLE 1

|  | Example 1 | Example 2 | Example 3 | Example 4 | Example 5 | Comparative Example 1 | Comparative Example 2 |
|---|---|---|---|---|---|---|---|
| Length of polymer chain (nm) | 2500 | 3000 | 4500 | 2000 | 2000 | — | — |
| Lubricity | 4.7 | 4.8 | 4.9 | 4.3 | 4.2 | 1 | 4.2 |
| Durability | 4.6 | 4.7 | 4.7 | 4.1 | 4.1 | 1 | 2.4 |
| Rate of decrease | 2% | 2% | 4% | 5% | 2% | 0% | 43% | alkali metal salt of 2-acrylamide-2-methylpropanesulfonic acid, and a compound represented by the following formula (1)

(1)

wherein $R^{11}$ represents —H or —CH$_3$; X represents —O—, —NH—, or —N$^+$—; m denotes an integer of 1 or more; and Y represents a zwitterionic or halogen group.

3. The method according to claim 1, wherein the step 1 comprises adsorbing a photopolymerization initiator on the surface of the object, and optionally then irradiating the surface with ultraviolet light having a wavelength within the range of 300 to 400 nm, to form the polymerization initiation points from the photopolymerization initiator on the surface.

4. The method according to claim 1, wherein the method comprises inserting an inert gas into a reaction container, a reaction tube, and a reaction solution during or before the light irradiation, and polymerizing the monomer in an atmosphere replaced with the inert gas.

5. The method according to claim 1, wherein the (liquid) deliquescent monomer or a solution thereof contains a polymerization inhibitor, and is polymerized in the presence of the polymerization inhibitor.

6. The method according to claim 5, wherein the polymerization inhibitor is 4-methylphenol.

7. The method according to claim 1, wherein the polymer chains each have a length within the range of 10 to 50000 nm.

8. A catheter, formed by the method according to claim 1.

9. A catheter, which is formed by the method according to claim 1 and is required to have lubricity in the presence of water.

10. A catheter, comprising a three-dimensional solid at least partially having a surface modified by the method according to claim 1.

11. A method for producing a catheter of a rubber vulcanizate or a thermoplastic elastomer, the method comprising:
step 1 of forming polymerization initiation points on a surface of the catheter; and
step 2 of radically polymerizing a deliquescent monomer in the presence of a photopolymerization initiator starting from the polymerization initiation points by irradiation with ultraviolet light having a wavelength within the range of 300 to 400 nm, to grow polymer chains on the surface of the catheter,
wherein the photopolymerization initiator is at least one of a benzophenone compound and a thioxanthone compound represented by the following formulas wherein $R^1$ to $R^5$ and $R^{1'}$ to $R^{5'}$ are the same as or different from one another and each represent a hydrogen atom, an alkyl group, a halogen, a hydroxyl group, a primary to tertiary amino group, or a mercapto group, wherein $R^6$ to $R^9$ and $R^{6'}$ to $R^{9'}$ are the same as or different from one another and each represent a hydrogen atom, a halogen atom, or an alkyl, cyclic alkyl, aryl, alkenyl, alkoxy, or aryloxy group.

12. A method for producing a catheter of a rubber vulcanizate or a thermoplastic elastomer, the method comprising
step I of radically polymerizing a deliquescent monomer in the presence of a photopolymerization initiator by irradiation with ultraviolet light having a wavelength within the range of 300 to 400 nm, to grow polymer chains on a surface of the catheter,
wherein the photopolymerization initiator is at least one of a benzophenone compound and a thioxanthone compound represented by the following formulas wherein $R^1$ to $R^5$ and $R^{1'}$ to $R^{5'}$ are the same as or different from one another and each represent a hydrogen atom, an alkyl group, a halogen, a hydroxyl group, a primary to tertiary amino group, or a mercapto group, wherein $R^6$ to $R^9$ and $R^{6'}$ to $R^{9'}$ are the same as or different from one another and each represent a hydrogen atom, a halogen atom, or an alkyl, cyclic alkyl, aryl, alkenyl, alkoxy, or aryloxy group.

13. A method for producing a fender of a rubber vulcanizate or a thermoplastic elastomer, the method comprising:
step 1 of forming polymerization initiation points on a surface of the fender; and
step 2 of radically polymerizing a deliquescent monomer starting from the polymerization initiation points by irradiation with ultraviolet light having a wavelength within the range of 300 to 400 nm, to grow polymer chains on the surface of the fender.

14. A method for producing a fender of a rubber vulcanizate or a thermoplastic elastomer, the method comprising
step I of radically polymerizing a deliquescent monomer in the presence of a photopolymerization initiator by irradiation with ultraviolet light having a wavelength within the range of 300 to 400 nm, to grow polymer chains on a surface of the fender.

15. The method according to claim 14, wherein the photopolymerization initiator is at least one of a benzophenone compound and a thioxanthone compound.

16. A fender, at least partially having a groove surface modified by the method according to claim 13.

* * * * *